United States Patent
Bilton et al.

(10) Patent No.: US 10,286,155 B2
(45) Date of Patent: May 14, 2019

(54) PEN-TYPE DRUG INJECTION DEVICE WITH DOSE SETTING AND RE-SETTING MECHANISM

(71) Applicant: Sanofi, Paris (FR)

(72) Inventors: Simon Lewis Bilton, Warwickshire (GB); David Aubrey Plumptre, Worcestershire (GB); Matthew Jones, Warwick (GB); Joseph Butler, Warwickshire (GB)

(73) Assignee: Sanofi, Paris (FR)

( * ) Notice: Subject to any disclaimer, the term of this patent is extended or adjusted under 35 U.S.C. 154(b) by 117 days.

(21) Appl. No.: 14/915,430

(22) PCT Filed: Sep. 3, 2014

(86) PCT No.: PCT/EP2014/068653
§ 371 (c)(1),
(2) Date: Feb. 29, 2016

(87) PCT Pub. No.: WO2015/032780
PCT Pub. Date: Mar. 12, 2015

(65) Prior Publication Data
US 2016/0206826 A1 Jul. 21, 2016

(30) Foreign Application Priority Data
Sep. 3, 2013 (EP) .................................... 13182759

(51) Int. Cl.
*A61M 5/315* (2006.01)
*A61M 5/20* (2006.01)
*A61M 5/31* (2006.01)

(52) U.S. Cl.
CPC .......... *A61M 5/31551* (2013.01); *A61M 5/20* (2013.01); *A61M 5/31535* (2013.01);
(Continued)

(58) Field of Classification Search
CPC .......... A61M 5/31551; A61M 5/31548; A61M 5/31535; A61M 5/31541; A61M 5/31583
See application file for complete search history.

(56) References Cited

U.S. PATENT DOCUMENTS

| 2005/0055011 A1 | 3/2005 | Enggaard |
| 2007/0129687 A1* | 6/2007 | Marshall ................ A61M 5/20 604/207 |

(Continued)

FOREIGN PATENT DOCUMENTS

| EP | 1926514 | 12/2008 |
| EP | 1819382 | 10/2009 |

(Continued)

OTHER PUBLICATIONS

International Search Report and Written Opinion in International Application No. PCT/EP2014/068653, dated Oct. 23, 2014, 14 pages.

(Continued)

*Primary Examiner* — Nathan R Price
*Assistant Examiner* — Tasnim Mehjabin Ahmed
(74) *Attorney, Agent, or Firm* — Fish & Richardson P.C.

(57) ABSTRACT

A pen type drug injection device includes a housing, a dose dial member, a torsion spring fixed between the housing and the dial member such that energy is accumulated in the torsion spring upon rotation of the dial member relative to the housing, a drive member engaging a lead screw, a first clutch, and a second clutch. The first clutch couples the drive member and the housing, in a coupled state and allows relative rotation between them in a de-coupled state. The second clutch rotationally couples the drive member and the dial member in a coupled state and allows clockwise and anti-clockwise rotation between them in a de-coupled state. The second clutch includes a ratchet clicker with teeth having different tooth angles in the clockwise and the anti-clockwise direction, such that, in the de-coupled state, the teeth override each other with different resistance in opposite directions.

18 Claims, 7 Drawing Sheets

Figure 1:
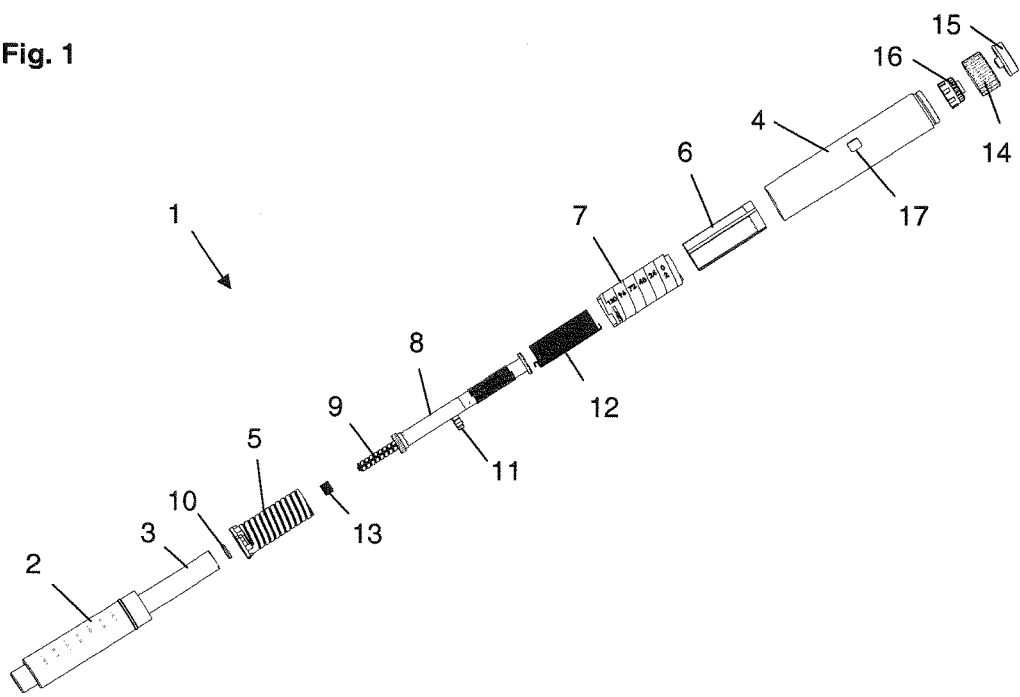

(52) U.S. Cl.
CPC .... *A61M 5/31541* (2013.01); *A61M 5/31553* (2013.01); *A61M 5/31583* (2013.01); *A61M 5/31528* (2013.01); *A61M 5/31586* (2013.01); *A61M 5/31593* (2013.01); *A61M 2005/202* (2013.01); *A61M 2005/2073* (2013.01); *A61M 2005/3126* (2013.01); *A61M 2205/581* (2013.01); *A61M 2205/582* (2013.01)

(56) References Cited

U.S. PATENT DOCUMENTS

| | | | |
|---|---|---|---|
| 2008/0306445 | A1 | 12/2008 | Burren et al. |
| 2009/0254035 | A1 | 10/2009 | Kohlbrenner et al. |
| 2012/0197213 | A1* | 8/2012 | Kohlbrenner ........... A61M 5/20 604/220 |
| 2012/0239066 | A1* | 9/2012 | Levine ........... A61B 17/320758 606/159 |

FOREIGN PATENT DOCUMENTS

| | | |
|---|---|---|
| EP | 1909870 | 3/2011 |
| EP | 2606924 | 6/2013 |
| JP | 2009-507581 | 2/2009 |
| JP | 2010-503434 | 2/2010 |
| RU | 2011/148399 | 6/2013 |
| WO | WO 2005/053778 | 6/2005 |
| WO | WO2007/030957 | 3/2007 |
| WO | WO 2007/063342 | 6/2007 |
| WO | WO2008/031235 | 3/2008 |
| WO | WO 2010/066590 | 6/2010 |
| WO | WO 2010/127146 | 11/2010 |
| WO | WO 2011/089246 | 7/2011 |
| WO | WO2013/098194 | 7/2013 |

OTHER PUBLICATIONS

International Preliminary Report on Patentability in International Application No. PCT/EP2014/068653, dated Mar. 8, 2016, 9 pages.

* cited by examiner

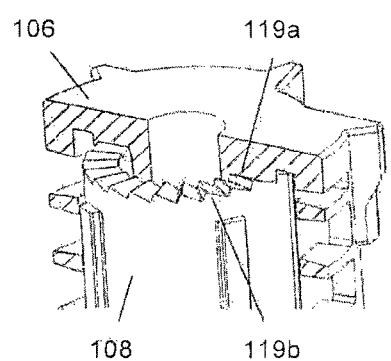
Fig. 11
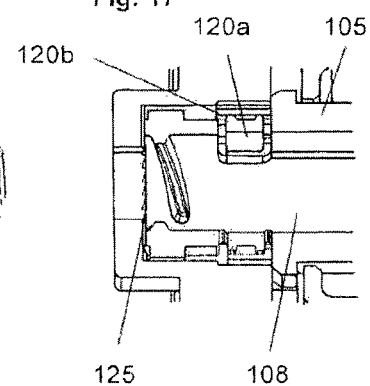
Fig. 17
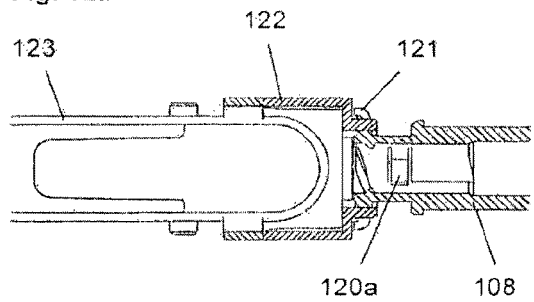
Fig. 12a
Fig. 12b
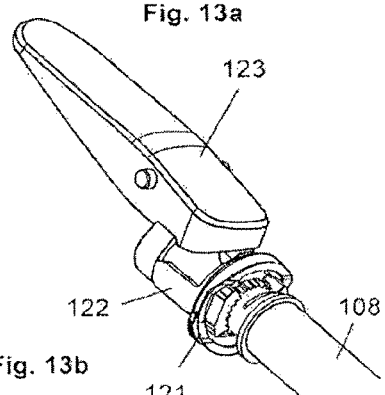
Fig. 13a
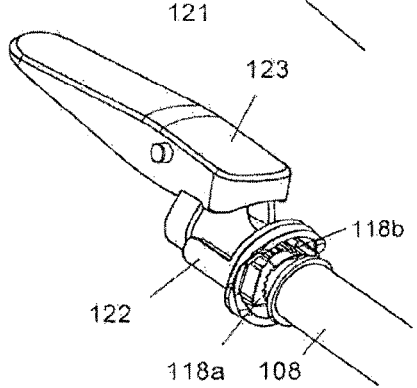
Fig. 13b

PEN-TYPE DRUG INJECTION DEVICE WITH DOSE SETTING AND RE-SETTING MECHANISM

CROSS-REFERENCE TO RELATED APPLICATIONS

This application is a U.S. national stage application under 35 USC § 371 of International Application No. PCT/EP2014/068653, filed on Sep. 3, 2014, which claims priority to European Patent Application No. 13182759.4, filed on Sep. 3, 2013, the entire contents of which are incorporated herein by reference.

The present invention relates to a drive mechanism which is suitable for an injection device, especially a pen type drug delivery device. The mechanism comprises a housing, a dial member, a torsion spring fixed between the housing and the dial member such that energy is accumulated in the torsion spring upon rotation of the dial member relative to the housing, a drive member engaging a lead screw, a first clutch rotationally coupling the drive member and the housing in a coupled state and allowing relative rotation between the drive member and the housing in a de-coupled state, and a second clutch rotationally coupling the drive member and the dial member in a coupled state and allowing relative clockwise and anti-clockwise rotation between the drive member and the dial member in a de-coupled state.

An injection device as defined above is known e.g. from EP 1 819 382 B1 wherein the second clutch is provided as a self-tightening ratchet which has saw-toothed teeth with approximately vertical orientated flanks as the self-tightening flanks. In order to reset or reduce an already set dose, the dial member is arranged to be axially retractable over a distance corresponding to the height of the teeth of the one-way ratchet. Thus, by pulling the dial member back, and thereby disengaging the dial member from the drive member, an already set dose can be reduced or even reset. For some users the requirement of retracting the dial member prior to reset or reduce an already set dose is considered as a drawback. A further example of a similar drive mechanism including a torsion spring is known from EP 1 909 870 B1.

As an alternative to drive mechanisms including a torsion spring, drive mechanisms are known comprising a compression spring. An example of such an injection device is known from EP 1 926 514 B1 which further comprises a slipping clutch with a detent element and a counter detent element which come into a mutual positive and non-positive engagement in discrete latching positions during a movement in the dosing direction or in the correction direction. The detent element and the counter detent element are formed in such a way that in the latching engagement of the motion they at least apply a lower resistance to the motion in one of the directions than in the other. In order to dispense a set dose this known injection device requires to displace the detent element with respect to the counter detent element in an axial direction such that they come out of engagement, i.e. the slipping clutch is fully de-coupled.

WO 2008/031235 A1 discloses a drug delivery device which is driven by a spiral spring, i.e. a coiled strip of metal. The device comprises a ratchet with different ramped teeth such that a different resistance in the clockwise and anti-clockwise direction occurs during dose setting and dose resetting. Further, the device comprises several units which may be coupled or decoupled by clutches. A second unit of the device is mentioned as comprising a dose setting member, an inner ring and a ratchet ring. A clutch shaft is described as part of a third unit comprising the spiral spring. One of the clutches couples and decouples the spring and the drive unit.

WO 2013/098194 A2 mentions a ratchet with different teeth angles in the dial-up and dial-down rotation direction. During dose resetting the teeth are fully decoupled such that in this decoupled state there is no resistance at all irrespective of the direction of rotation.

Aspects of the invention may include an improved alternative to the above solutions. Aspects of the invention may include a drive mechanism which allows to easily reduce an already set dose.

The present invention is based on the idea to provide a detent engagement as the second clutch that resists spring torque but is overcome by the user dialing. According to a preferred embodiment, the second clutch comprises a ratchet clicker with teeth having in the clockwise and the anti-clockwise direction different ramped tooth angles such that the teeth are allowed to override each other in the de-coupled state of the second clutch with a different resistance in the clockwise and the anti-clockwise direction. To act as a ratchet clicker in its de-coupled state, the second clutch is arranged such that its teeth are in loose engagement in the de-coupled state. In other words, the second clutch is fully engaged in the coupled state preventing any relative rotation between the drive member and the dial member, whereas a relative rotation of the drive member relative to the dial member is possible in the de-coupled state with the teeth of the ratchet clicker overriding each other to provide a tactile and/or audible feedback to a user. Due to the different ramped tooth angles of the ratchet clicker teeth the sound generated by the teeth overriding each other may be different in the clockwise and the anti-clockwise direction.

A clutch according to the invention is a component or feature suitable for connecting two component parts either by form fit (positive fit), e.g. with teeth suitable for engaging and dis-engaging each other, or by a non-positive (frictional) connection or a combination thereof. A clutch may be formed by integral features of the two component parts which are to be coupled or de-coupled, for example by teeth, splines, grooves, abutment faces or the like directly provided on the component parts. Alternatively, a clutch may comprise one or more separate coupling parts which are, for example permanently, fixed or linked to the two component parts which are to be coupled or de-coupled. Actuation of a clutch, i.e. the act of coupling or decoupling, may include a relative movement of clutch parts or clutch features, for example foe dis-engaging clutch teeth, and/or may include a change in a force exerted on clutch parts or clutch features.

The general function of a drive mechanism as defined above is to set a dose and to subsequently dispense the set dose. Dose setting (dose dialing) usually requires a user to manipulate one element of the drive mechanism, preferably to rotate a dial member e.g. via a dial grip. During dose dispensing the dial member may move, e.g. rotate, back to its original position wherein a drive member, which is not actuated during dose setting is moved together with the dial member during dose dispensing. The movement of the drive member may be a rotation, a displacement or a combined movement e.g. along a helical path. The drive member may act on a lead screw which functions as a piston rod for expelling medicament from a cartridge during dose dispensing.

In addition to this basic function of a drive mechanism it is in some cases preferred to allow a resetting of an already set dose, i.e. a correction or a deselecting of a dose. Preferably the user simply has to rotate the dial member, e.g.

via a dial grip, in the opposite direction compared to the rotation during dose setting. Preferably, the drive member is not actuated during dose resetting, either.

To allow rotation of components of the mechanism, it is preferred if the components are mainly located concentrically about a common longitudinal axis of the drive mechanism. Thus, the components may have a tubular or sleeve-like shape. Further, although it is desirable to reduce the total number of components of a drive mechanism, it might be useful for manufacturing reasons to split one or more components into separate elements. For example, a housing may comprise an outer body and an insert and/or an inner body which is axially and/or rotationally constrained to the outer body. In addition, a clutch may be designed by providing protrusions and/or recesses directly on the components which are to be coupled or decoupled by the clutch. As an alternative, a separate clutch element may be provided interposed between the two components which have to be coupled or decoupled.

The present invention is directed to a drive mechanism which may be used in an injection device. An injection device usually further comprises a cartridge holder and a cartridge containing medicament to be dispensed. In a reusable injection device, the cartridge holder may be detachable from the drive mechanism to exchange an empty cartridge with a new one. As an alternative, in a disposable injection device the cartridge holder and the cartridge are firmly attached to the drive mechanism such that the whole injection device has to be discarded after a number of doses have been dispensed from the cartridge.

In the following, the distal end of an injection device or drive mechanism is referred to as the end where the cartridge and e.g. a needle are located, whereas the opposite end is the proximal end. A dose button may be provided at the proximal end.

According to one aspect of the present invention, the second clutch provided between the drive member and the dial member provides two functions: on the one hand, the second clutch allows or prevents relative rotation between the drive member and the dial member and on the other hand it provides a ratchet clicker in the de-coupled state of the second clutch. Thus, less parts or components are required for the drive mechanism according to the present invention.

In a preferred embodiment of the present invention the teeth of the ratchet clicker have a steeper ramped tooth angle in the rotational direction in which the torsion spring biases the dial member and have a shallower ramped tooth angle in the opposite rotational direction. The torsion spring of the drive mechanism accumulates energy upon rotation of the dial member relative to the housing and relative to the drive member. To store this accumulated energy, it is necessary to prevent the dial member from undesired back winding. This is achieved by the steeper ramped tooth angle of the ratchet clicker teeth which are designed such that the torque of the torsion spring is too small to force the teeth of the ratchet clicker to override each other in the coupled state and the de-coupled state of the second clutch. On the other hand, due to the shallower ramped tooth angle in the opposite rotational direction, the torque required by a user to set a dose, and thus straining the torsion spring, is relatively small. To reduce an already set dose, the user has to overcome the higher resistance of the steeper ramped tooth angle of the ratchet clicker teeth, however, this rotation to reduce a set dose is assisted by the torque of the torsion spring such that the overall user torque required to reduce a set dose is again relatively small. As an alternative to the different angles of slope or in addition thereto, the friction of the teeth may be different in the clockwise and the anti-clockwise direction. This may include different materials on the two faces of a tooth and/or different surface finish (e.g. different roughness).

Although different arrangements of the drive mechanism would be possible, it is preferred if during dose setting and dose resetting the first clutch is in its coupled state and the second clutch is in its de-coupled state. Thus, during dose setting and dose resetting the drive member is prevented from relative rotation with respect to the housing. This makes sure that the lead screw is not actuated during dose setting and dose resetting. However, the dial member may be rotated by a user overcoming the resistance of the second clutch which acts as a ratchet clicker. Preferably, the dial member rotates relative to the rotationally fixed drive member during dose setting and dose resetting.

To maintain this state of the first clutch and the second clutch during dose setting and dose resetting, it is preferred to bias the first clutch in its coupled state and/or the second clutch in its de-coupled state during dose setting and dose resetting. This may be achieved by the torsion spring and/or by an additional spring or elastic member. In an embodiment of the invention the biasing may act to pull the second clutch into its coupled state, which is not a permanent coupled state, i.e. it can be overcome with user applied torque.

According to an embodiment of the present invention the teeth of the second clutch (ratchet clicker) engage in the de-coupled state during dose setting and dose resetting but are allowed to override each other by an axial movement against the force of an elastic member. In other words, either the torsion spring or an additional spring or elastic member forces the teeth of the ratchet clicker into engagement even in the de-coupled state of the second clutch. However, in this de-coupled state of the second clutch a relative axial movement of the respective teeth is allowed such that the teeth can jump over each other.

During dose dispensing the first clutch is in its de-coupled state and the second clutch is in its coupled state. Thus, during dose dispensing rotation of the drive member relative to the housing is allowed as the first clutch is in its de-coupled state while a relative rotation between the drive member and the dial member is prevented as the second clutch is in its coupled state. The coupled state of the second clutch may be a state where the teeth of the ratchet clicker engage but are not allowed to override each other and/or to perform a relative axial movement as mentioned above with respect to the de-coupled state of the second clutch. Thus, the dial member preferably rotates during dose dispensing and entrains the drive member which actuates the lead screw.

There are different ways to couple or de-couple the first clutch. According to a preferred embodiment, the first clutch is coupled and de-coupled by axially displacing the drive member relative to the housing. As an alternative, the drive member may be rotated and/or a separate component may be moved relative to the housing, i.e. displaced and/or rotated. According to a further embodiment of the present invention, the drive mechanism comprises a trigger clutch which is held rotationally fixed and axially displaceable within the housing. The first clutch may be de-coupled by axially displacing the trigger clutch relative to the drive member.

To actuate the trigger clutch, the drive mechanism preferably comprises a trigger pivotably attached to the housing. The trigger may engage the trigger clutch such that swiveling of the trigger relative to the housing axially displaces the trigger clutch.

The first clutch may comprise releasable locking means provided either directly on the drive member and/or the housing or on one or more separate components connected to the drive member and/or the housing. Preferably, the first clutch comprises at least one spline on an outer surface of the drive member and at least one corresponding notch on an inner surface of the housing or on an inner surface of a housing insert. As an alternative, notches may be provided on an outer surface of the drive member while an inner surface of the housing is provided with corresponding splines. In other words, the first clutch is preferably provided radially with respect to the drive member and the housing.

Generally, the second clutch may be provided in a similar way as described above with respect to the first clutch. However, it is preferred if the second clutch comprises face teeth on a front edge, e.g. a proximal surface, of the drive member and corresponding face teeth on a front edge, e.g. a distal surface, of the dial member or on a distal surface of a separate component like a clutch plate. Further, the face teeth may be provided on a flange or shoulder of the drive member and/or the dial member or a clutch plate. Thus, the second clutch is provided rather axially with respect to the drive member and the dial member.

According to one embodiment of the present invention a clutch plate is provided which is rotationally fixed to the dial member. The clutch plate may be further axially fixed to the dial member. The clutch plate forms part of the second clutch wherein the second clutch is coupled and de-coupled by axially displacing the clutch plate relative to the drive member. In other words, the second clutch may be coupled by pressing the clutch plate firmly to the drive member to prevent the teeth of the ratchet clicker from overriding each other.

According to a further aspect of the present invention, the drive mechanism comprises a display member which is guided in threaded engagement within the housing. The display member is preferably rotationally fixed to the dial member and displaceable relative to the dial member in an axial direction. For example corresponding splines and grooves may be provided on the display member and the dial member. The display member is marked with a sequence of numbers which are visible through a window or an aperture in the housing to denote the dialed dose. In addition, the display member may have the function of providing end stops for dose setting, dose resetting and/or dose dispensing. In other words, the display member may be moved between two positions defining a zero dose stop and a maximum settable dose stop.

According to a further aspect of the present invention, the display member may comprise a flexible element wherein the housing or the trigger clutch may comprise a counter element. The flexible element may contact the counter element at the end of dose dispensing to create an audible and/or tactile feedback. Thus, the flexible element and the counter element together indicate that dose dispensing is completed. Preferably, the counter element is provided on the trigger clutch such that upon swiveling of the trigger relative to the housing the counter element is moved into the path which is described by the flexible element of the display member during dose dispensing. The feedback at the end of dose dispensing is thus only provided if the trigger is actuated.

According to a further aspect of the present invention, the drive mechanism further comprises a nut which is guided axially displaceable and non rotatable on the drive member. For example, the nut and the drive member are provided with corresponding splines and notches. The nut further has an external thread engaging an internal thread of the dial member such that relative rotation between the drive member and the dial member during dose setting and dose resetting causes the nut to move towards an end stop. According to the present invention an injection device may comprise a cartridge containing a medicament and a drive mechanism as mentioned above. The nut and the end stop may be provided in the drive mechanism of the injection device such that the nut prevents setting of a dose exceeding the amount of a medicament in the injection device. In other words, the end stop preferably defines the length of a track on which the nut travels during dose setting, wherein the length of the track corresponds to the total amount of medicament in the cartridge. The internal thread of the dial member may be provided on an inner surface of the dial member and preferably comprises a plurality of thread segments.

According to a further aspect of the present invention, the housing further comprises a unidirectional ratchet or preferably helical stop features cooperating with the drive member wherein the drive member and the lead screw are in threaded engagement. The helical stop features preferably have a helical pitch which is (at least approximately) matched to the helical pitch of the threaded engagement of the drive member and the lead screw. Thus, the drive member rotates along a helical path defined by the helical stop feature profile and thus travels helically up the lead screw which remains stationary relative to the housing. The spacing of the helical stop features corresponds to the drive member rotation required to deliver a single unit of medicament. Hence, when the drive member is rotated by one unit, axial separation is generated corresponding to the lead screw displacement required to dispense one unit. The axial force provided by the torsion spring which is applied to the drive member acts directly on the lead screw tending to displace the drive member and lead screw to reengage the helical stop features. The stop feature interface improves dose accuracy as they provide a consistent lead screw axial position which is insensitive to variation in the rotational position of the drive member as defined by the first clutch.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-idecanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Figure 2:
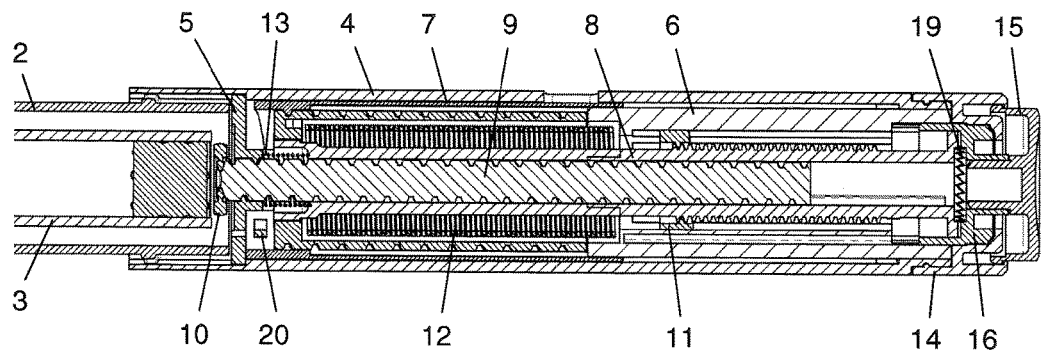
Figure 3:
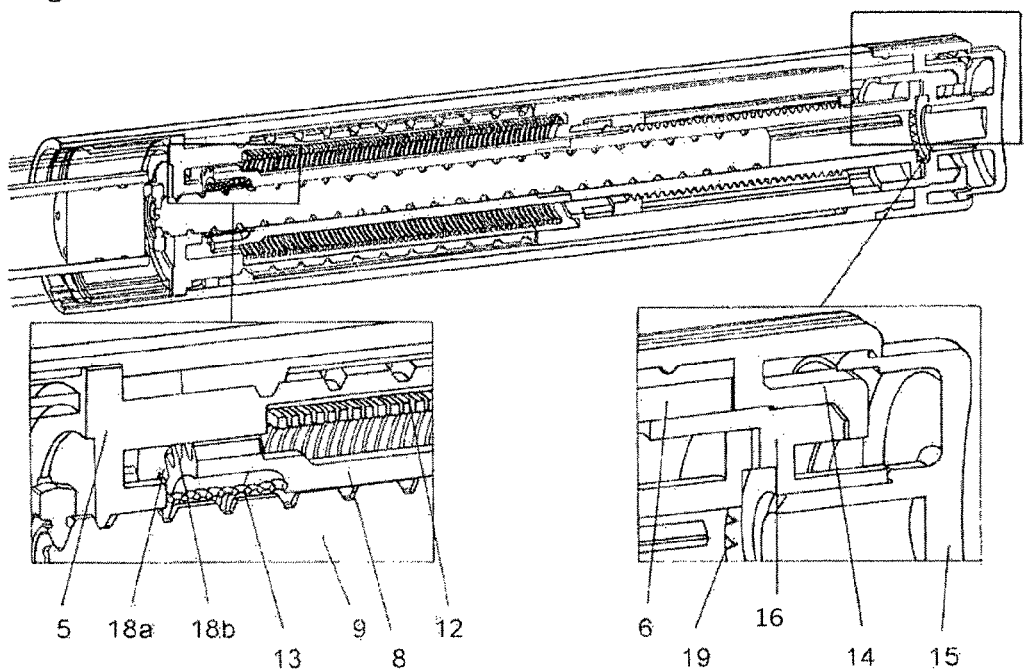
Figure 4:
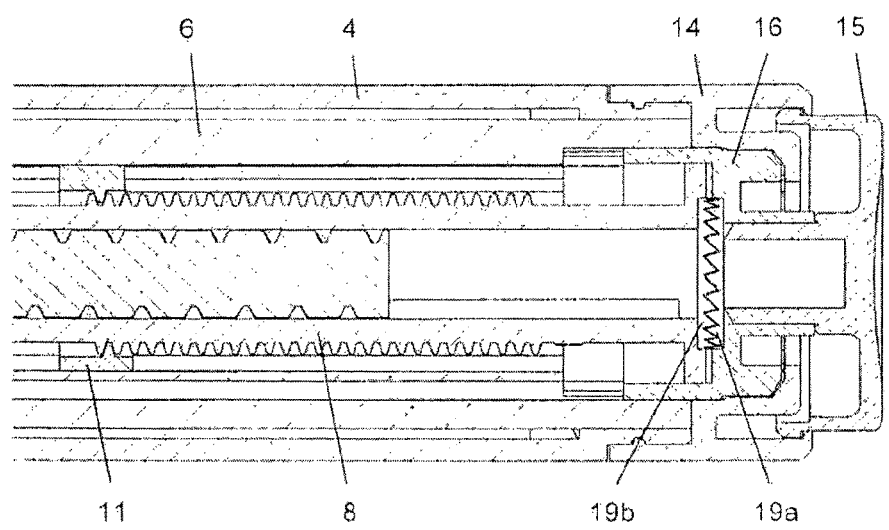
Figure 5A:
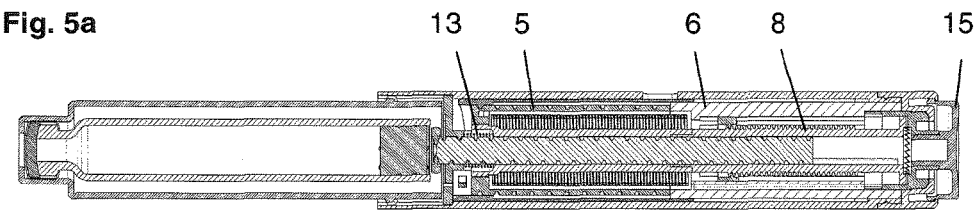
Figure 5B:
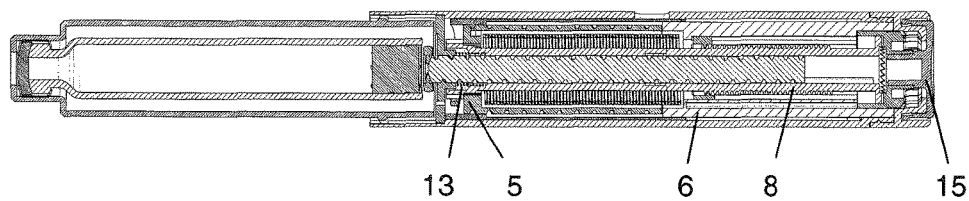
Figure 6:
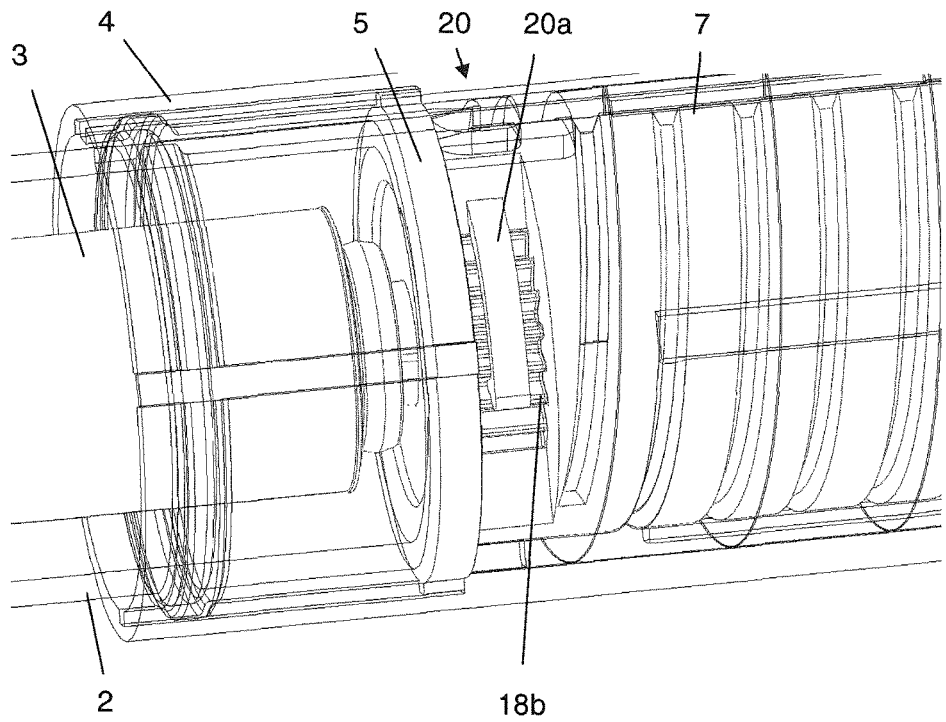
Figure 7:
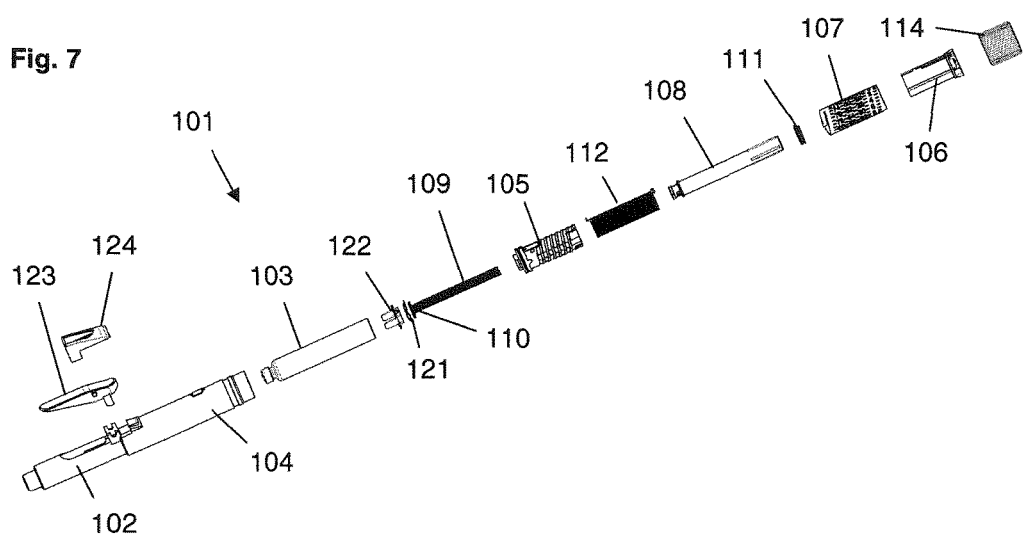
Figure 8:
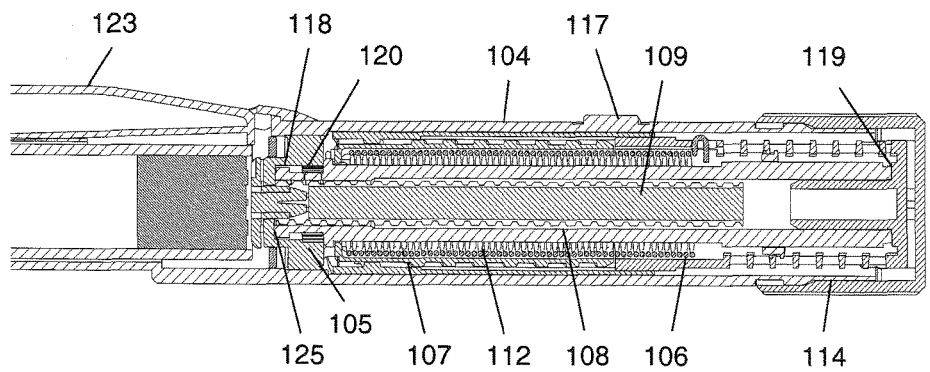
Figure 9:
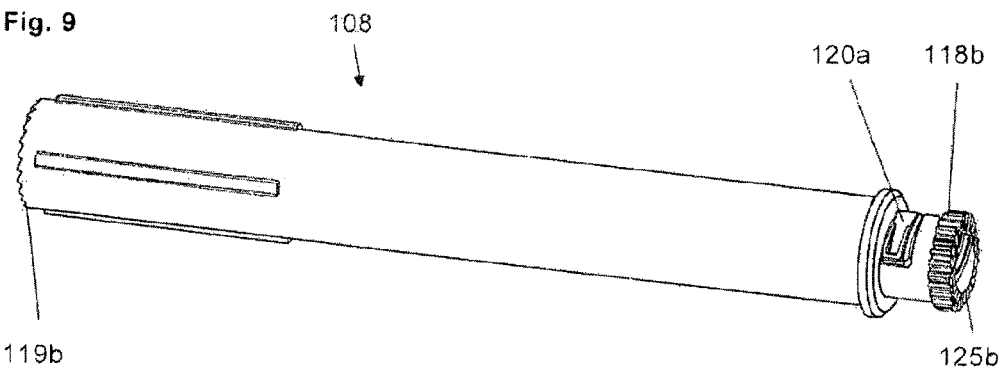
Figure 10A:
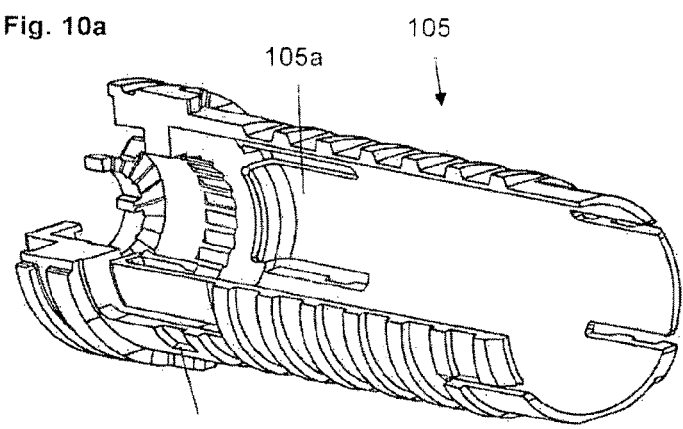
Figure 10B:
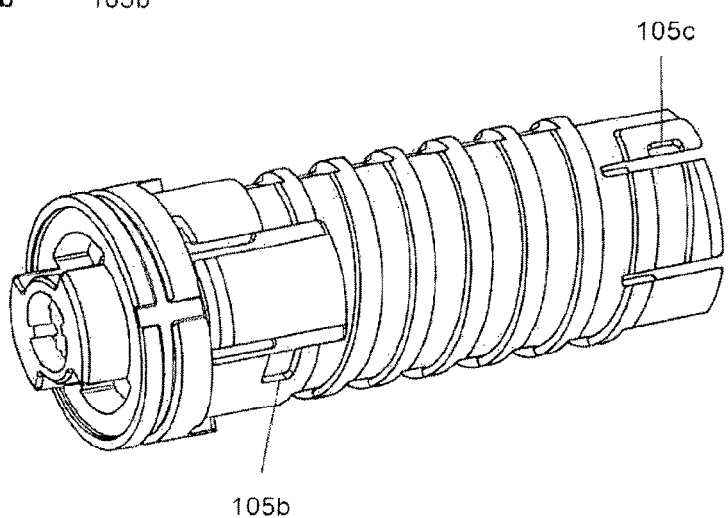
Figure 14:
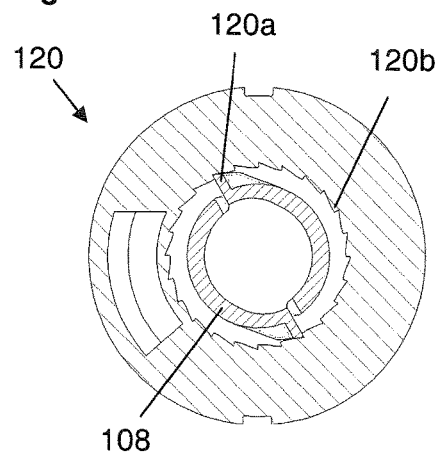
Figure 15:
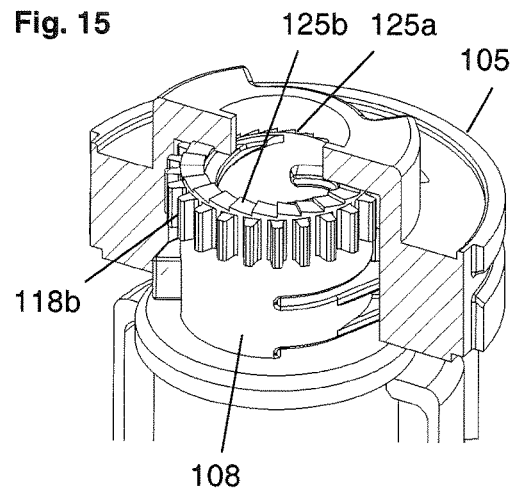
Figures 16A, 16B, 16C:
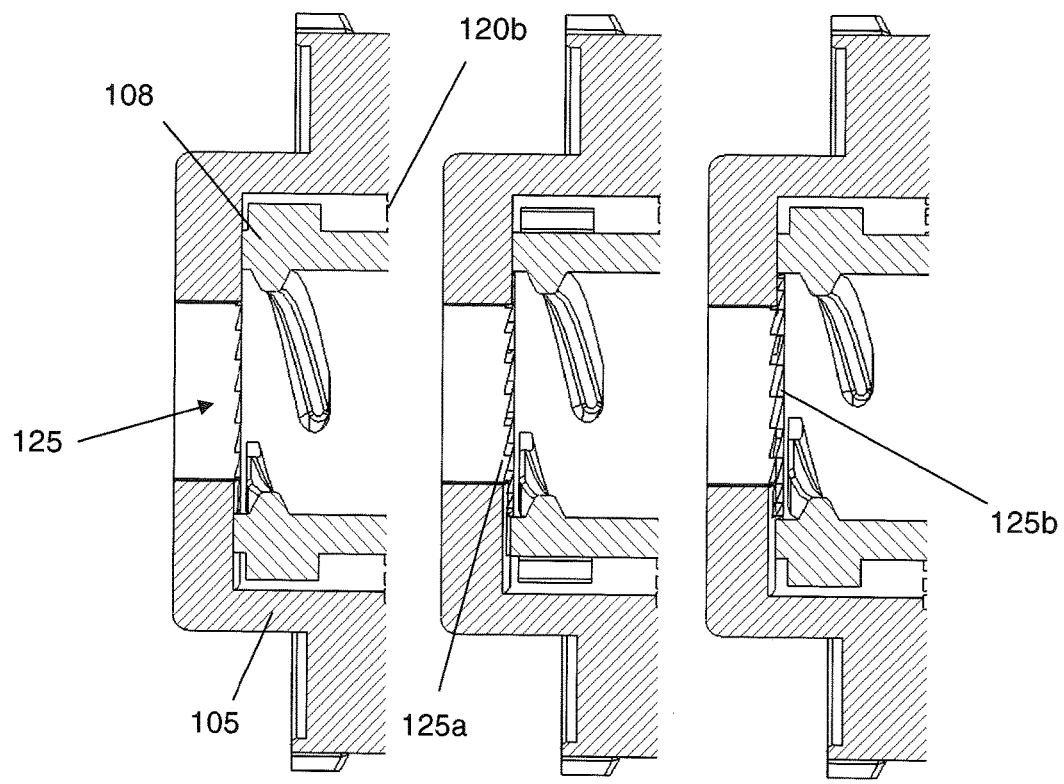

The present invention will now be described in further detail with reference to the accompanying schematic drawings, wherein FIG. 1 shows an exploded view of an injection device comprising a drive mechanism according to a first embodiment of the invention, FIG. 2 shows a section view of the drive mechanism of FIG. 1, FIG. 3 shows a further section view of the drive mechanism of FIG. 1 with two enlarged details, FIG. 4 shows a section view of a further detail of the drive mechanism of FIG. 1, FIGS. 5a, 5b show further section views of the drive mechanism in different states, FIG. 6 shows a perspective view of components of the drive mechanism of FIG. 1, FIG. 7 shows an exploded view of an injection device with a drive mechanism according to a second embodiment of the invention, FIG. 8 shows a section view of the drive mechanism of FIG. 7, FIG. 9 shows a section view of the drive member of the drive mechanism of FIG. 7, FIGS. 10a, 10b show perspective views of the inner body of the drive mechanism of FIG. 7, FIG. 11 shows a detail of the drive member and the dial member of the drive mechanism of FIG. 7, FIGS. 12a, 12b show section views of two states of a trigger of the drive mechanism of FIG. 7, FIGS. 13a, 13b show perspective views of two states of the trigger according to FIGS. 12a, 12b, FIG. 14 shows a section view of the drive mechanism of FIG. 7, FIG. 15 shows a detail of the drive member of the drive mechanism of FIG. 7, FIGS. 16a to 16c show section views of a ratchet of the drive mechanism of FIG. 7 in different positions, FIG. 17 shows a further detail of the drive member of the drive mechanism of FIG. 7.

An injection device 1 according to the present invention is shown in FIG. 1 in an exploded view. The injection device 1 comprises a cartridge holder 2, a cartridge 3 and a drive mechanism. The drive mechanism comprises an outer housing 4, an inner housing 5, a dose dial sleeve as a dial member 6, a number sleeve as a display member 7, a drive sleeve as a drive member 8, a lead screw 9, a bearing 10, a nut 11, a drive spring 12, a return spring 13, a dial grip 14, a dose button 15 and a clutch plate 16. All components are located concentrically about a common principle axis of the mechanism. In more detail, the drive member 8 surrounds the lead screw 9, the torsion spring 12 surrounds the drive member 8, the dial member 6 and the inner housing 4 surround the torsion spring 12, the display member 7 surrounds the dial member 6 and the inner housing 5 and the outer housing 4 surrounds the display member 7. Further, the nut 11 and the clutch plate 16 are located between the drive member 8 and the dial member 6.

The dose button 15 is axially constrained to the clutch plate 16. As can be seen in FIG. 2, this may be achieved by a snap-on connection with the clutch plate 16 having an opening for receiving a pin of the dose button 15. Thus, the dose button 15 may be rotatable with respect to the clutch plate 16.

The dial grip 14 is axially constrained to the outer housing 4 which forms a body for the drive mechanism. Again, as shown in FIG. 3, this may be achieved by a snap-on connection between the dial grip 14 and the outer housing 4. The dial grip 14 is rotationally constrained to the clutch plate 16. In the embodiment of FIGS. 1 to 6 a splined interface is provided between the dial grip 14 and the clutch plate 16. This splined interface is disconnected when the dose button 15 is pressed, i.e. when the dose button 15 and the clutch plate 16 are moved axially relative to the dial grip 14 and the outer housing 4.

The clutch plate 16 is further rotationally constrained to the dial member 6. Again, a splined interface may be provided between the clutch plate 16 and the dial member 6. The clutch plate 16 is further coupled to the drive member 8 via a ratchet interface which occurs on axial abutment. The ratchet interface provides a detented position between the dial member 6 and the drive member 8 corresponding to each dose unit and engages different ramped tooth angles during clockwise and anti-clockwise relative rotation between the dial member 6 and the drive member 8. This ratchet interface forms the second clutch 19 with corresponding teeth 19a, 19b provided on the clutch plate 16 and the drive member 8, respectively.

The display member 7 is rotationally constrained to the dial member 6. Again, a splined interface may be provided between the display member 7 and the dial member 6. The display member 7 is further constrained to move along a helical path relative to the inner housing 5. This may be achieved by a threaded interface between the display member 7 and the inner housing 5. As an alternative, a threaded interface may be provided between display member 7 and the outer housing 4. The display member 7 is marked with a sequence of numbers which are visible through a window 17 in the outer housing 4. As an alternative to a transparent window an aperture could be provided in the outer housing 4. The window 17 allows the user to denote the dialed dose of medicament. The window 17 may be or may comprise a magnifying lens. The window 17 may be an integral part of the outer housing 4 or a separate component attached to the housing.

The nut 11 acts as a last dose nut and is interposed between the dial member 6 and the drive member 8. The nut 11 is rotationally constrained to the dial member 6, e.g. via a splined interface. Thus, the nut 11 may be axially displaced relative to the dial member 6. The nut 11 moves along a helical path relative to the drive member 8, e.g. via a threaded interface, when relative rotation occurs between the dial member 6 and the drive member 8, i.e. during dose setting and dose resetting. An end stop (not shown) may be provided to limit the movement of the nut 11 in the track defined by the threaded interface. As an alternative, the nut may be splined to the drive member 8 and threadedly engaged with the dial member 6.

The drive member 8 extends from the interface from the dial member 6 down to a splined tooth interface with the inner housing 5. This provides rotational constraint of the drive member 8 to the inner housing 5. The releasable splined tooth interface between the drive member 8 and the inner housing 5 forms the first clutch 18 with teeth 18a, 18b provided on the dial member 6 and the drive member 8, respectively.

When the dose button 15 is pressed, the splined teeth of the first clutch 18 are disengaged and a ratchet feature 20 is engaged which provides an audible and/or tactile feedback during dose dispensing.

The inner housing 5 is rigidly fixed to the outer housing 4. Thus, neither any rotation nor any axial movement between the inner housing 5 and the outer housing 4 is possible. The inner housing 5 and the outer housing 4 may be formed as one integral part, however due to manufacturing reasons it is preferred to provide the housing as the two separate components of the outer housing 4 and the inner housing 5.

The drive spring 12 is a torsion spring which is attached at one end to the inner housing 5 and at the other end to the dial member 6. The drive spring 12 is pre-wound upon assembly, such that it applies a torque to the dial member 6 when the mechanism is at zero units dialed. The action of rotating the dial grip 14 to set a dose rotates the dial number 6 relative to the inner housing 5 and winds up the drive spring 12.

The lead screw 9 is rotationally constrained to the drive member 8 e.g. via a splined interface. When rotated, the lead screw 9 is forced to move axially relative to the drive member 8. This is achieved by a threaded interface between the lead screw 9 and the inner housing 5. The bearing 10 is axially constrained to the lead screw 9 and acts on the bung within the cartridge 3 during dose dispensing.

The axial position of the drive member 8, the clutch plate 16 and the dose button 15 is defined by the action of the return spring 13 which abuts the inner housing 5 and applies a force on the drive member 8 in the proximal direction. This ensures that the clutch plate 16 is in splined engagement with the dial grip 14 and that the drive member 8 is in splined engagement with the inner housing 5. The return spring 13 also acts to maintain the engagement of the ratchet features between the drive member 8 and the clutch plate 16, i.e. to maintain the engagement of the second clutch 19. As an alternative, the function of the return spring 13 may be achieved fully or in part by the torsion spring 12.

The outer housing 4 provides location for the cartridge 3 and the cartridge holder 2 which can be attached to the outer housing 4. Further, the outer housing 4 comprises an interface to rigidly constrain the inner housing 5 and a groove on its external surface to axially retain the dial grip 14. Further, a removable cap may be provided which fits over the cartridge holder 2 and is retained via clip features.

In the following, the functions and interactions of the above mentioned components will be described in more detail together with an explanation of the use of the drive mechanism of the injection device 1.

Regarding the first clutch 18 and the second clutch 19 there are two generally distinct states of the drive mechanism of the injection device 1 which are shown in FIGS. 5a and 5b, respectively. FIG. 5a shows the drive mechanism in an at rest condition which is a condition if a user does not exert any forces on the drive mechanism. In this at rest condition the first clutch 18 couples the drive member 8 to the inner housing 5 and the second clutch 19 allows a relative rotation between the clutch plate 16 and the drive member 8. However, to rotate the clutch plate 16 with respect to the drive member 8, a torque has to be provided to overcome the resistance of the ratchet feature, i.e. the clutch plate 6 is not freely rotatable with respect to the drive member 8. The second condition which is shown in FIG. 5b occurs if a user depresses dose button 15. This decouples the first clutch 18 such that the drive member 8 is free to rotate with respect to the inner housing 5 and the second clutch 19 is coupled to prevent a relative rotation between the drive member 8 and the clutch plate 16.

With the device in the at rest condition, the display member 7 is positioned against its zero dose abutment with the inner housing 5 and the dose button 15 is not depressed. A dose marking "0" on the dial member 7 is visible through the window 17 on the outer housing 4. The drive spring 12 which has a number of pre-wound turns applied to it during assembly of the device applies a torque to the dial member 6. The dial member 6 is prevented from rotating under the action of the torque by its ratchet interface (second clutch 19) with the drive member 8. The drive member 8 is prevented from rotating by the interlock provided by the engagement of splined teeth 18a, 18b on the drive member 8 and the inner housing 5 (first clutch 18). This is shown in FIG. 3. As can be seen in the enlarged details of FIG. 3, return spring 13 maintains the first clutch 18 in its coupled state by pushing the drive member 8 in the proximal direction. However, the drive member 8 is free to be displaced in the distal direction against the force of the return spring 13 as the teeth 19a, 19b of the second clutch 19 override each other upon a relative rotation between the drive member 8 and the clutch plate 16. As can be seen in FIG. 3, the height of the teeth of the second clutch 19 is smaller than the axial height (or length) of the splines of the first clutch 18. Thus, the first clutch 18 remains in its coupled state even if the teeth of the second clutch 19 override each other.

The user selects a variable dose of medicament by rotating the dial grip 14 clockwise which generates an identical rotation in the dial member 6. Rotation of the dial member 6 causes wind up of the drive spring 12, increasing the energy stored within it. The drive member 8 is still prevented from rotating due to the engagement of its splined teeth 18a, 18b with the inner housing 5 (first clutch 18 coupled). A relative rotation must therefore occur between the clutch plate 16 and the drive member 8 via the ratchet interface of the second clutch 19.

The user torque required to rotate the dial grip 14 is a sum of the torque required to wind up the drive spring 12 and the torque required to overhaul the ratchet feature of the second clutch 19. The return spring 12 is designed to provide an axial force to the ratchet feature and to bias the components (drive member 8, clutch plate 16, dose button 15) away from the cartridge end of the injection device 1. The axial load acts to maintain engagement of the ratchet teeth 19a, 19b of the clutch plate 16 and the drive member 8. The torque required to overhaul the ratchet teeth is resultant from the axial load applied by the return spring 13, the clockwise ramp angle of the ratchet, the friction coefficient between the mating surfaces and the mean radius of the ratchet features.

As the user rotates the dial grip 14 sufficiently to increment the mechanism by one unit, the dial member 6 rotates relative to the drive member 8 by one set of ratchet teeth 19a, 19b. At this point the ratchet teeth reengaged into the next detented position. An audible click is generated by the ratchet reengagement, and tactile feedback is given by the change in torque input required. Thus, the second clutch 19 forms a ratchet clicker.

Relative rotation of the dial member 6 and the drive member 8 causes a last dose nut 11 to travel along its threaded path towards its last dose abutment on the drive member 8. Rotation of the dial member 6 further generates rotation in the display member 7, which travels along its helical path defined by its interface with the inner housing 5. The dose marking corresponding to x units become aligned to the window 17 in the outer housing 4. The device is now set to deliver x units of liquid medicament.

With no user torque applied to the dial grip 14, the dial member 6 is now prevented from rotating under the action of the torque applied by the drive spring 12, solely by the ratchet engagement between the clutch plate 16 and the drive member 8 (second clutch 19). The torque necessary to overhaul the ratchet in the anti-clockwise direction is resultant from the axial load applied by the return spring 13, the anti-clockwise ramp angle of the ratchet, the friction coefficient between the mating surfaces and the mean radius of the ratchet features. The torque necessary to overhaul the ratchet must be greater than the torque applied to the dial member 6 (and hence clutch plate 16) by the drive spring 12. The ratchet ramp angle is therefore increased in the anti-clockwise direction to ensure this is the case.

The user may now choose to increase the selected dose by continuing to rotate the dial grip 14 in the clockwise direction. The process of overhauling the ratchet interfaces between the dial member 6 and the drive member 8 is repeated for each dose unit. Additional energy is stored within the drive spring 12 for each dose unit and audible and tactile feedback is provided for each unit dialed by the reengagement of the ratchet teeth. The torque required to rotate the dial grip 14 increases as the torque required to wind up the drive spring 12 increases. The torque required to overhaul the ratchet in the anti-clockwise direction must therefore be greater than the torque applied to the dial member 6 by the drive spring 12 when the maximum dose has been reached.

If the user continues to increase the selected dose until the maximum dose limit is reached, the display member 7 engages with its maximum dose abutment on the outer housing 4, which prevents further rotation of the display member 7, dial member 6, clutch plate 16 and dial grip 14. At this point the maximum dose marking on the display member 7 is aligned to the window 17 in the outer housing 4.

Depending on how many units have already been delivered by a drive mechanism, during selection of a dose, the last dose nut 11 may contact its last dose abutment, i.e. the end stop with the drive member 8. The abutment prevents further relative rotation of the dial member 6 and the drive member 8 and therefore limits the dose that can be selected. The position of the last dose nut 11 is determined by the total number of relative rotations between the dial member 6 and the drive member 8, which have occurred each time the user sets a dose.

With the mechanism in a state in which a dose has been selected, the user is able to deselect or reset any number of units from this dose. Deselecting a dose is achieved by the user rotating the dial grip 14 anti-clockwise. The torque applied to the dial grip 14 by the user is sufficient, when combined with the torque applied by the drive spring 12 to overhaul the ratchet 19 between the clutch plate 16 and the drive member 8 in the anti-clockwise direction. When the ratchet is overhauled, anti-clockwise rotation occurs in the dial member 6 (via the clutch plate 16) which returns the display member 7 towards the zero dose position, and unwinds the drive spring 12. The relative rotation between the dial member 6 and the drive member 8 causes the last dose nut 11 to return along its helical path, away from the last dose abutment.

With the mechanism in a state in which a dose has been selected, the user is able to activate the drive mechanism to commence delivery of a dose (dose dispensing). Delivery of a dose is initiated by the user depressing the dose button 15 on the top (proximal end) of the drive mechanism. When the dose button is depressed, it moves axially, acting on the clutch plate 16, which in turn acts on the drive member 8. The clutch plate 16 disengages its spline teeth from the dial grip 14 and after that the drive member 8 disengages its spline teeth (first clutch 18) from the inner housing 5.

When the splined interface of the first clutch 18 between the inner housing 5 and the dive member 8 disengages, the interface which prevents rotation of the drive member 8 during selection of a dose is removed. The torque applied to the dial member 6 from the drive spring 12 is transmitted, via the ratchet interface of the second clutch 19 into the drive member 8. This torque causes the drive member 8 and hence, due to its relative engagement with the inner housing 5, advancement of the lead screw 9. Axial displacement of the lead screw 9 forces liquid medicament to be delivered from the mechanism, by the action of the bearing 10 which contacts and displaces the bung within the cartridge 3.

The ratchet feature 20 of the inner housing 5 comprises a clicker arm 20a. As can be taken from FIG. 6, the clicker arm 20a is a compliant cantilever beam integrated into the inner housing 5, which interfaces radially with the spline ratchet teeth 18b in the drive member 8. The ratchet teeth 18b spacing corresponds to the drive member 8 rotation required to deliver a single dose unit. During dispense, as the drive member 8 rotates, the spline features engage with the clicker arm 20a to produce an audible click with each dose unit delivered. The torque required to overhaul the clicker arm is resultant from the ratchet teeth profile, the stiffness of the cantilever beam and the nominal interference between the clicker arm and the ratchet. The clicker arm interface is designed such that the torque required to overhaul is significantly less than the torque provided by the drive spring 12.

The rotation of the dial member 6 also causes the display member 7 to return along its helical path, relative to the inner housing 5, towards the zero dose abutment. Delivery of a dose continues via the mechanical interactions described above while the user continues to depress the dose button 15. If the user releases the dose button 15, the return spring 13 returns the dose button 15 to its at rest position via the drive member 8 and the clutch plate 16 such that the drive member 8 becomes rotationally constrained and delivery of a dose is halted.

With the dose button 15 depressed, delivery of a dose continues until the display member 7 reaches its zero dose abutment with the inner housing 5. The torque applied to the dial member 6 is reacted by the abutment of the display member 7 and the dial member 6, wherein the clutch plate 16 and the drive member 8 are prevented from rotating further. During delivery of a dose, the drive member 8 and the dial member 6 rotate together, so that no relative motion in the last dose nut 11 occurs. The last dose nut 11 therefore travels towards its abutment on the drive member 8 during dose setting only and travels away from the end stop during dose resetting.

Once the delivery of a dose is stopped by the display member 7 returning to the zero dose abutment, the user may release the dose button 15 which will reengage the first clutch 18 between the inner housing 5 and the drive member 8. The mechanism is now returned to the at rest condition.

It is possible to angle the spline teeth 18a, 18b on either the drive member 8 or inner housing 5 so that when the dose button 15 is released the reengagement of the spline teeth fractionally backwind the drive member 8 thereby removing the engagement of the display member 7 to the zero dose stop abutment in the inner housing 5. This removes the effect of clearances in the drive mechanism (for example due to tolerances) which could otherwise lead to slight advancement of the lead screw 9 and medicament dispense when the drive mechanism is dialed for the subsequent dose. This is due to the zero dose stop of the display member 7 no longer restraining the mechanism and instead the restraint returning to the splines between the drive member 8 and the inner housing 5.

A second embodiment of a drive mechanism which is suitable for an injection device 101 is shown in FIGS. 7 to 17. The injection device 101 comprises a cartridge holder 102, a cartridge 103 containing a medicament, optionally a cap (not shown) and a drive mechanism. The drive mechanism comprises an outer housing 104 with a window 117, an inner housing 105, a dial member 106 (dial sleeve), a display member 107 (number sleeve), a drive member 108 (drive sleeve), a lead screw 109, a bearing 110, a nut 111, a torsion spring 112, a dial grip 114, a first clutch 118, a second clutch 119, a ratchet feature 120, a clutch spring 121, a trigger clutch 122, a trigger 123 and a trigger cover 124.

Similar to the first embodiment, all components, except for the trigger 123 and the trigger cover 124, are located concentrically about a common principal axis of the drive mechanism.

The dial grip 114 is axially constrained to the outer housing 104. It is rotationally constrained, via a splined interface, to the dial member 106. As shown in FIG. 11, the dial member 106 is coupled to the drive member 108 via a ratchet interface (second clutch 119), which occurs on an axial abutment. The ratchet provides a detented position between the dial member 106 and the drive member 108 corresponding to each dose unit, and engages different ramped tooth angles during clockwise and anti-clockwise relative rotation. Corresponding ratchet teeth 119a, 119b are provided on facing surfaces of the dial member 106 and the drive member 108.

The display member 107 is rotationally constrained, via a splined interface, to the dial member 106. It is constrained to move along a helical path, relative to the inner housing 105, via a threaded interface. The display member 107 is marked with a sequence of numbers, which are visible through the window 117 in the outer housing 104, to denote the dialed dose of medicament.

The last dose nut 111 is located between the dial member 106 and the drive member 108. It is rotationally constrained to the drive member 108, via a splined interface. It moves along a helical path relative to the dial member 106, via a threaded interface, when relative rotation occurs between the dial member 106 and drive member 108.

The drive member 108 extends from the interface with the dial member 106 down to a ratchet interface with the inner housing 105, which occurs on an axial abutment. The ratchet interface defines the axial position of the drive member 108 at the end of dose delivery, and is included to improve dose accuracy. The drive member 108 is rotationally constrained to the trigger clutch 122, via engagement of a set of spline teeth, when the trigger 123 is activated. It provides a clicker arm 120a, which acts radially against a set of ratchet teeth 120b in the inner housing 105. It moves along a helical path relative to the lead screw 109, via a threaded interface. The drive member 108 provides an axial abutment with the inner housing 105, which engages when the drive mechanism dispenses, to react the force applied by the lead screw 109 to the cartridge 103.

The torsion spring 112 is attached at one end to the inner housing 105 and at the other end to the dial member 106. The attachments at both ends are configured to transfer tangential forces, resulting from torsion of the spring 112, and axial forces along the primary axis of the drive mechanism (longitudinal axis). The torsion spring 112 is pre-wound upon assembly, such that it applies a torque to the dial member 106 when the mechanism is at zero units dialed. The action of rotating the dial grip 114, to set a dose, rotates the dial grip 114 relative to the inner housing 105, and winds up the torsion spring 112. The torsion spring 112 is designed in such a way as to exert an axial force which acts to pull the dial member 106 towards the inner housing 105.

The lead screw 109 is rotationally constrained to the inner housing 105 via a splined interface. The lead screw 109 is forced to move axially relative to the inner housing 105, through its threaded interface to the drive member 108, when the drive member 108 moves relative to the inner housing 105. The bearing 110 (washer) is axially constrained to the lead screw 109 and acts on the bung within the liquid medicament cartridge 103.

The inner housing 105 is rigidly constrained to the outer housing 104. As shown in FIGS. 10a, 10b the axial abutment with the drive member 108 is provided by a pair of compliant arms 105a which deflect during assembly. A pair of abutment features 105b, 105c is provided, at either end of the threaded interface with the display member 107, which limit the range of travel of the display member 107. These abutments 105b, 105c provide the zero dose and maximum dose stops. The inner housing 105 provides a rotational constraint to the trigger clutch 122, and provides an axial abutment which reacts the axial force generated by the clutch spring 121. The axial position of the trigger clutch 122 is defined by the action of the clutch spring 121, which forces the trigger clutch 122 towards the cartridge end (distal end) of the drive mechanism, and its abutment with the trigger 123. When axially positioned in its at rest position, the trigger clutch 122 engages with the spline teeth on the drive member 108 which constrains the rotation of the drive member 108. The spline teeth 118a on the trigger clutch 122 and the corresponding spline teeth 118b on the drive member 108 form the first clutch 118. Engagement and disengagement of the first clutch 118 is shown in FIGS. 12a to 13b in more detail.

The clutch spring 121 is located between the inner housing 105 and the trigger clutch 122 and acts to force the trigger clutch 122 towards the cartridge end of the drive mechanism. The trigger 123 is constrained to pivot in the outer housing 104. It has an integral spring element, which acts to rotate the trigger 123 away from the outer housing 104. When the trigger 123 is depressed, an abutment is created with the trigger clutch 122, which moves the trigger clutch 122 axially towards the inner housing 105.

The outer housing 104 provides location for the liquid medication cartridge 103, the pivot for the trigger 123, an interface to rigidly constrain the inner housing 105, a window 117 through which the dose number on the display member 107 can be viewed, and a groove on its external surface to axially retain the dial grip 114. The trigger cover 124 may clip into the outer housing 104, and retains the trigger 123 within its pivot interface with the outer housing 104. The removable cap fits over the cartridge holder element 102 and is retained onto the outer housing 104 via clips when the drive mechanism is not in use. When the cap is fitted onto the outer housing 104, a mechanical interlock is created with the trigger 123, which prevents the trigger from being depressed from its at rest position.

With the device in the at rest condition, the display member 107 is positioned against its zero dose abutment with the inner housing 105 and the trigger 123 is not depressed. Dose marking '0' on the display member 107 is visible through the window 117 on the outer housing 104. The torsion spring 112, which has a number of pre-wound turns applied to it during assembly of the drive mechanism, applies a torque to the dial member 106. The dial member 106 is prevented from rotating, under the action of this torque, by its ratchet interface (second clutch 119) with the drive member 108, and by the abutment of the display member 107 against the inner housing 105. The drive member 108 is prevented from rotating by the interlock provided by the engagement of splined teeth 118a, 118b on the drive member 108 and trigger clutch 122, respectively.

The user selects a variable dose of liquid medicament by rotating the dial grip 114 clockwise, which generates an identical rotation in the dial member 106. Rotation of the dial member 106 causes wind up of the torsion spring 112, increasing the energy stored within the torsion spring 112. The drive member 108 is still prevented from rotating, due to the engagement of its splined teeth 118b with the trigger clutch 122. Relative rotation must therefore occur between the dial member 106 and drive member 108, via the ratchet interface (second clutch 119).

The user torque required to rotate the dial grip 114 is a sum of torque required to wind up the torsion spring 112, and the torque required to overhaul the ratchet feature. The torsion spring 112 is designed such that it applies an axial load to the dial member 106. The axial load acts to maintain the detented engagement of the dial member 106 and drive member 108. The torque required to overhaul the ratchet is resultant from the axial load applied by the torsion spring 112, the clockwise ramp angle of the ratchet, the friction coefficient between the mating surfaces and the mean radius of the ratchet feature.

As the user rotates the dial grip 114 sufficiently to increment the mechanism by 1 unit, the dial member 106 rotates relative to the drive member 108 by 1 set of ratchet teeth 119a, 119b. At this point the ratchet teeth 119a, 119b reengage into the next detented position. An audible click is generated by the ratchet re-engagement, and tactile feedback is given by the change in torque profile.

Relative rotation of the dial member 106 and the drive member 108 causes the last dose nut 111 to travel along its threaded path, towards its last dose abutment.

Rotation of the dial member 106 generates rotation in the display member 107, which travels along its helical path defined by its interface with the inner housing 105. The dose marking corresponding to 1 unit becomes aligned to the window 117 in the outer housing. The device is now set to deliver 1 unit of liquid medicament.

With no user torque applied to the dial grip 114, the dial member 106 is now prevented from rotating, under the action of the torque applied by the torsion spring 112, solely by the ratchet engagement between the dial member 106 and the drive member 108. The torque necessary to overhaul the ratchet in the anti-clockwise direction is resultant from the axial load applied by the torsion spring 112, the anti-clockwise ramp angle of the ratchet, the friction coefficient between the mating surfaces and the mean radius of the ratchet feature. The torque necessary to overhaul the ratchet must be greater than the torque applied to the dial member 106 by the torsion spring 112. The ratchet ramp angle is therefore increased in the anti-clockwise direction to ensure this is the case.

The user may now choose to increase the selected dose by continuing to rotate the dial grip 114 in the clockwise direction. The process of overhauling the ratchet interfaces (teeth 119a, 119b) between the dial member 106 and drive member 108 is repeated for each dose unit. Additional energy is stored within the torsion spring 112 for each dose unit and audible and tactile feedback is provided for each unit dialed by the re-engagement of the ratchet teeth 119a, 119b. Thus, the second clutch 119 forms a clicker ratchet. The torque required to rotate the dial grip 114 increases as the torque required to wind up the torsion spring 112 increases. To torque required to overhaul the ratchet in the anti-clockwise direction must therefore be greater than the torque applied to the dial member 106 by the torsion spring 112 when the maximum dose has been reached.

If the user continues to increase the selected dose until the maximum dose limit is reached, the display member 107 engages with its maximum dose abutment 105c on the inner housing 105, which prevents further rotation of the display member 107, dial member 106 and dial grip 114. At this point the maximum dose marking on the display member 107 is aligned to the window 117.

Depending on how many units have already been delivered by the drive mechanism, during selection of a dose, the last dose nut 111 may contact its last dose abutment with the dial member 106. The abutment prevents further relative rotation of the dial member 106 and the drive member 108, and therefore limits the dose that can be selected. The position of the last dose nut 111 is determined by the total number of relative rotations between the dial member 106 and drive member 108, which have occurred each time the user sets a dose.

With the drive mechanism in a state in which a dose has been selected, the user is able to deselect any number of units from this dose. Deselecting a dose is achieved by the user rotating the dial grip 114 anti-clockwise. The torque applied to the dial grip 114 by the user is sufficient, when combined with the torque applied by the torsion spring 112, to overhaul the ratchet 119a, 119b between the dial member 106 and drive member 108 in the anti-clockwise direction. When the ratchet is overhauled, anti-clockwise rotation occurs in the dial member 106, which returns the display member 107 towards the zero dose position, and unwinds the torsion spring 112. The relative rotation between the dial member 106 and drive member 108 causes the last dose nut 111 to return along its helical path, away from the last dose abutment 105c.

With the mechanism in a state in which a dose has been selected, the user is able to activate the drive mechanism to commence delivery of a dose. Delivery of a dose is initiated by the user depressing the trigger 123 on the side of the drive mechanism. If the cap is fitted to the drive mechanism, a mechanical interlock is provided which prevents depression of the trigger 123, and therefore prevents the drive mechanism from dispensing a dose. Selection of a dose can therefore be completed with the cap fitted, and this eliminates the risk of the drive mechanism dispensing a dose by unintentional depression of the trigger 123 while the user is selecting the dose. In addition, this feature allows the device to be stored or carried with a pre-selected dose, perhaps by a career or parent, ready to use without dialing.

Once the cap is removed, depression of the trigger 123 can occur. As the trigger is depressed, an abutment is created with the trigger clutch 122 which acts to move the trigger clutch axially away from the cartridge 103, against the action of the clutch spring 121. When the trigger 123 is fully depressed, sufficient axial travel has occurred in the trigger clutch 122 to remove the engagement of the spline teeth 118a, 118b on the trigger clutch 122 and the drive member 108.

When this splined interface between the trigger clutch 122 and the drive member 108 disengages, the interface which prevented rotation of the drive member 108 during selection of a dose has been removed. The torque applied to the dial member 106 from the torsion spring 112 is transmitted, via the ratchet interface (second clutch 119), into the drive member 108. This torque acts to overhaul the clicker arm 120a between the drive member 108 and the inner housing 104, and the axial ratchet interface between the drive member 108 and the inner housing 104.

As shown in FIGS. 14 and 17, the clicker arm 120a is a compliant cantilever beam integrated into the drive member 108, which interfaces radially with a set of ratchet teeth 120b in the inner housing 105. The ratchet teeth spacing corresponds to the drive member 108 rotation required to deliver a single dose unit. The clicker arm 120a produces an audible click to the user, corresponding to each dose unit delivered. The torque required to overhaul the clicker arm 120a is resultant from the ratchet teeth 120b profile, the stiffness of the cantilever beam and the nominal interference between clicker arm and ratchet. The clicker arm interface is designed such that the torque required to overhaul is significantly less than the torque provided by the torsion spring 112.

As shown in FIGS. 15 to 17, further ratchet 125 is provided as helical stop features between a shoulder of the inner housing 105 and an end face of the drive member 108. These helical stop features comprise corresponding teeth 125a, 125b provided on the inner housing and the drive member. The torque required to overhaul the helical stop features 125, between the drive member 108 and the inner housing 105, is resultant from the axial load applied by the torsion spring 112, the ramp angle of the helical stop features (teeth 125a, 125b), the friction coefficient between the mating surfaces and the mean radius of the helical stop features. The helical stop features 125 are designed such that the torque required to overhaul is significantly less than the torque provided by the torsion spring 112.

The torque applied to the drive member 108 by the torsion spring 112 is sufficient to overhaul the clicker arm 120a and helical stop features 125. The drive member 108 starts to rotate along a helical path defined by the ramp profile of the helical stop features. The ramp profile is matched to the helical pitch of the threaded interface between the drive member 108 and the lead screw 109, such that the drive member 108 travels helically up the lead screw 109, which remains stationary relative to the inner housing 105.

The dial member 106 rotates with the drive member 108, which causes the display member 107 to return along its helical path, relative to the inner housing 105, towards the zero dose abutment 105b.

The spacing of the teeth 125a, 125b (helical stop features) corresponds to the drive member 108 rotation required to deliver a single unit of liquid medicament. When the drive member 108 has rotated by 1 unit, axial separation is generated between the teeth 125a, 125b corresponding to the lead screw 109 displacement required to dispense 1 unit. The axial force provided by the torsion spring 112, which is applied to the drive member 108, acts directly on the lead screw 109, tending to displace the drive member 108 and the lead screw 109 to re-engage the helical stop features 125.

If a greater axial force is required to displace the lead screw 109 than directly provided by the torsion spring 112, the drive member 108 continues to rotate along its helical path, defined by the threaded interface with the lead screw 109, until an axial abutment is created between the drive member 108 and the inner housing 105. The drive member 108 is now constrained axially, and further helical motion between the drive member 108 and lead screw 109 results in rotation only of the drive member 108 causing axial motion of the lead screw 109 relative to the inner housing 105.

The torque applied to the drive member 108 from the torsion spring 112 is converted into an axial force via the threaded interface with the lead screw 109. The axial force generated is sufficient to displace the lead screw 109 relative to the inner housing 105. Axial displacement of the lead screw 109 forces liquid medicament to be delivered from the drive mechanism, by the action of the washer bearing 110, which is axially constrained to the lead screw 109, contacting and displacing the bung within the cartridge 103.

Delivery of a dose continues via the mechanical interactions described above while the user continues to depress the trigger 123. If the user releases the trigger 123, the integral spring returns the trigger 123 to its at rest position and the clutch spring 121 forces the splined teeth 118a on the trigger clutch 122 to re-engage with the teeth 118b on the drive member 108. The drive member 108 becomes rotationally constrained and delivery of a dose is halted.

With the trigger 123 depressed, delivery of a dose continues until the display member 107 reaches the zero dose abutment 105b with the inner housing 105. The torque applied to the dial member 108 is reacted by the abutment of the display member 107 and the dial member 106 and drive member 108 are prevented from rotating further.

The axial force from the torsion spring 112 is still applied to the dial member 106 and drive member 108, and the drive member 108 and lead screw 109 displace axially together to complete the dose, which re-engages the axial ratchet or helical stop interface 125 between the drive member 108 and inner housing 105. The helical stop interface 125 improves dose accuracy as it provides a consistent lead screw axial position which is insensitive to variation in the rotational position of the drive member as defined by the first clutch 118. This removes the effect of clearances in the drive mechanism (for example due to tolerances) which could otherwise lead to slight advancement of the lead screw 109 and medicament dispense when the drive mechanism is dialed for the subsequent dose. This is due to the zero dose stop of the display member 107 no longer restraining the mechanism and instead the restraint returning to the splines between the drive member 108 and the inner housing 105.

During delivery of a dose, the drive member 108 and dial member 106 rotate together, so that no relative motion in the last dose nut 111 occurs. The last dose nut 111 therefore travels towards its abutment on the dial member 106 during dialing only.

Once the delivery of a dose is stopped, by the display member 107 returning to the zero dose abutment 105b, the user may release the trigger 123, which will re-engage the trigger clutch spline teeth 118a with the drive member 108. The drive mechanism is now returned to the at rest condition.

The drive mechanism enables a one piece body construction, as all coaxial components can be installed into the outer housing from the dial grip end. The mechanism allows a sub-assembly containing the pre-wound torsion spring 112 to be assembled, prior to final assembly into a device containing the liquid medicament cartridge 103. The washer bearing 110 provides an abutment which retains the trigger clutch 122 in engagement with the drive member 108 at the sub-assembly stage. Once fully assembled, the trigger clutch 122 is restrained by abutments with the outer housing 104 or the trigger 123.

REFERENCE NUMERALS 1, 101 injection device
2, 102 cartridge holder
3, 103 cartridge
4, 104 outer housing (body)
5, 105 inner housing
105a compliant arm
105b zero dose abutment
105c maximum dose abutment
6, 106 dial member (dose dial sleeve)
7, 107 display member (number sleeve)
8, 108 drive member (drive sleeve)
9, 109 lead screw
10, 110 bearing (washer)
11, 111 last dose nut
12, 112 drive spring (torsion spring)
13 return spring
14, 114 dial grip
15 dose button
16 clutch plate
17, 117 window
18, 118 first clutch
18a, 18b spline teeth
118a, 118b spline teeth
19, 119 second clutch (clicker ratchet)
19a, 19b ratchet teeth
119a, 119b ratchet teeth
20, 120 ratchet (clicker)
20a, 120a clicker arm
120b clicker teeth
121 clutch spring
122 trigger clutch
123 trigger
124 trigger cover
125 helical stop features
125a, 125b teeth

The invention claimed is:

1. A drive mechanism for an injection device, the drive mechanism comprising:
   a housing,
   a dial member,
   a torsion spring fixed between the housing and the dial member and configured to accumulate energy upon rotation of the dial member relative to the housing,
   a drive member engaging a lead screw,
   a nut which is guided axially displaceably and non-rotatably on the drive member and which has an external thread engaging an internal thread of the dial member such that relative rotation between the drive member and the dial member during dose setting causes the nut to move towards an end stop, wherein the nut is configured to prevent setting of a dose exceeding an amount of a medicament in the injection device, a first clutch rotationally coupling the drive member and the housing in a coupled state and allowing relative rotation between the drive member and the housing in a de-coupled state, and a second clutch rotationally coupling the drive member and the dial member in a coupled state and allowing relative clockwise and anti-clockwise rotation between the drive member and the dial member in a de-coupled state, wherein the second clutch comprises a ratchet clicker with teeth having in a clockwise direction and an anti-clockwise direction different ramped tooth angles such that the teeth are allowed to override each other in the de-coupled state of the second clutch with a different resistance in the clockwise direction and the anti-clockwise direction, and wherein the teeth of the ratchet clicker comprises first face teeth on a front edge of the drive member directed in a proximal direction and second face teeth on a front edge of the dial member directed in a distal direction.

2. The drive mechanism according to claim 1, wherein the teeth have a steeper ramped tooth angle in a rotational direction in which the torsion spring biases the dial member and have a shallower ramped tooth angle in a second rotational direction.

3. The drive mechanism according to claim 1, wherein the teeth have a higher friction coefficient in a first rotational direction in which the torsion spring biases the dial member and have a lower friction coefficient in a second rotational direction.

4. The drive mechanism according to claim 1, wherein during dose setting and dose resetting the first clutch is in its coupled state and the second clutch is in its de-coupled state.

5. The drive mechanism according to claim 1, wherein during dose setting and dose resetting the torsion spring and/or an additional spring biases the first clutch in its coupled state and/or pulls the second clutch in its de-coupled state.

6. The drive mechanism according to claim 1, wherein during dose setting and dose resetting the teeth of the second clutch engage in the de-coupled state but are allowed to override each other by an axial movement against a force of an elastic member.

7. The drive mechanism according to claim 1, wherein during dose dispensing the first clutch is in its de-coupled state and the second clutch is in its coupled state.

8. The drive mechanism according to claim 1, wherein the first clutch is coupled and de-coupled by axially displacing the drive member relative to the housing.

9. The drive mechanism according to claim 1, further comprising a trigger clutch which is held rotationally fixed and axially displaceable within the housing, wherein the first clutch is de-coupled by axially displacing the trigger clutch relative to the drive member.

10. The drive mechanism according to claim 9, further comprising a trigger pivotably attached to the housing, wherein the trigger engages the trigger clutch such that swiveling of the trigger relative to the housing axially displaces the trigger clutch.

11. The drive mechanism according to claim 1, wherein the first clutch comprises splines on an outer surface of the drive member and corresponding notches on an inner surface of the housing.

12. The drive mechanism according to claim 1, further comprising a clutch plate rotationally fixed to the dial member, wherein the second clutch is coupled and de-coupled by axially displacing the clutch plate relative to the drive member.

13. The drive mechanism according to claim 1, further comprising a display member in threaded engagement with the housing, wherein the display member is rotationally fixed to the dial member and displaceable relative to the dial member in an axial direction.

14. The drive mechanism according to claim 1, wherein the housing comprises helical stop features cooperating with the drive member, wherein the drive member and the lead screw are in threaded engagement.

15. The drive mechanism according to claim 1, wherein the first clutch comprises splines on an outer surface of the drive member and corresponding notches on an inner surface of a housing insert.

16. The drive mechanism according to claim 1, wherein the second clutch comprises face teeth on a front edge of the drive member and corresponding face teeth on a front edge of a clutch plate.

17. A drug delivery device comprising:
a cartridge holder configured to receive a cartridge; and
a drive mechanism comprising:
a drive mechanism housing,
a dial member,
a torsion spring fixed between the drive mechanism housing and the dial member and configured to accumulate energy upon rotation of the dial member relative to the drive mechanism housing,
a drive member engaging a lead screw,
a nut which is guided axially displaceable and non-rotatable on the drive member and which has an external thread engaging an internal thread of the dial member such that relative rotation between the drive member and the dial member during dose setting causes the nut to move towards an end stop, wherein the nut is configured to prevent setting of a dose exceeding an amount of a medicament in the drug delivery device,
a first clutch rotationally coupling the drive member and the drive mechanism housing in a coupled state and allowing relative rotation between the drive member and the drive mechanism housing in a de-coupled state, and
a second clutch rotationally coupling the drive member and the dial member in a coupled state and allowing relative clockwise and anti-clockwise rotation between the drive member and the dial member in a de-coupled state, wherein the second clutch comprises a ratchet clicker with teeth having in a clockwise direction and an anti-clockwise direction different ramped tooth angles such that the teeth are allowed to override each other in the de-coupled state of the second clutch with a different resistance in the clockwise direction and the anti-clockwise direction, wherein the teeth of the ratchet clicker comprises first face teeth on a front edge of the drive member directed in a proximal direction and second face teeth on a front edge of the dial member directed in a distal direction;
wherein the accumulated energy in the torsion spring can advance the lead screw to expel medicament from the cartridge.

18. A method of operating a drug delivery device, the method comprising:
rotating a dial member clockwise to set a dose of a drug to be delivered while a rotation of a drive member with respect to a housing is prevented with a first clutch, wherein rotating the dial member clockwise comprises causing energy in a drive spring to be stored,
causing a nut to axially move towards an end stop relative to the drive member without rotating relative to the drive member such that the set dose is prevented from exceeding an amount of a medicament in the drug delivery device, and
causing second face teeth of ratchet teeth of a second clutch to advance relative to first face teeth of the ratchet teeth of the second clutch to generate tactile feedback, the ratchet teeth of the second clutch preventing opposite rotation of the dial member under the energy of the drive spring and enabling the opposite rotation of the dial member when a user applies a force in an opposite direction, wherein the first face teeth are on a front edge of the drive member directed in a proximal direction, and the second face teeth are on a front edge of the dial member directed in a distal direction; and
pressing a dose button to deliver the dose, the pressing decoupling the drive member from the housing with the first clutch and, when decoupled, the dial member transferring the energy of the drive spring to the drive member via the second clutch to deliver the dose.

* * * * *

UNITED STATES PATENT AND TRADEMARK OFFICE
CERTIFICATE OF CORRECTION

PATENT NO. : 10,286,155 B2
APPLICATION NO. : 14/915430
DATED : May 14, 2019
INVENTOR(S) : Simon Lewis Bilton et al.

It is certified that error appears in the above-identified patent and that said Letters Patent is hereby corrected as shown below:

In the Claims

In Column 23, Line 23, in Claim 2, after "a" insert -- first --.

Signed and Sealed this
Twenty-seventh Day of August, 2019

Andrei Iancu
*Director of the United States Patent and Trademark Office*